United States Patent [19]

Wang et al.

[11] Patent Number: 5,672,696
[45] Date of Patent: Sep. 30, 1997

[54] TREATMENT OF PARAFFIN EMBEDDED TISSUE FOR GENE ANALYSIS

[75] Inventors: Lu Wang; Kazunari Hirayasu, both of Amagasaki, Japan

[73] Assignee: Wako Pure Chemical Industries, Ltd., Osaka, Japan

[21] Appl. No.: 498,775

[22] Filed: Jul. 5, 1995

[30] Foreign Application Priority Data

Jul. 6, 1994 [JP] Japan .................................. 6-177578

[51] Int. Cl.⁶ .............................. C07H 1/06; C07H 1/08
[52] U.S. Cl. .................. 536/25.42; 536/25.4; 536/25.41
[58] Field of Search .......................... 536/25.41, 25.42, 536/25.4

[56] References Cited

FOREIGN PATENT DOCUMENTS 5-508658  12/1993  Japan .

OTHER PUBLICATIONS

J. Finke et al.; Chemical Abstracts, vol. 119, No. 5, Aug. 29, 1993; p. 217, No. 42 089s; & Biotechniques 1993, 14(3), 448–53.
G.M. Rupp et al.; Chemical Abstracts, vol. 108, No. 17, Apr. 25, 1988; p. 392, No. 146 656p; & Biotechniques 1988, 6(1), 56–60.
G. Stanta et al.; Chemical Abstracts, vol. 117, No. 17, Oct. 26, 1992; p. 201, No.164 929v; & Biotechniques 1991, 11(3), 304, 306, 308.
A. Warford et al.; Chemical Abstracts, vol. 109, No. 5, Aug. 1, 1988; p. 180, No. 33 187p; & J. Pathol. 1988, 154(4), 313–20.
Biochemical and Biophysical, Research Communications, vol. 130, No. 1, pp. 118–126 (1985).
Experimental Medicine, vol. 8, No. 9, pp. 84–88 (1990).
Cancer Research, 46, pp. 2964–2969 (1986).
Laboratory Medicine, vol. 22, No. 8, pp. 543–546 (1991).
Am. J. Pathol., vol. 135, No. 4, pp. 697–702 (1989).
J. Invest. Dermatol., vol. 93, No. 1, pp. 183–187.
Am. J. Pathol., vol. 136, No. 3, pp. 541–548 (1990).
Bio Techniques, vol. 11, No. 3, pp. 372–377 (1991).
J. Exp. Med., vol. 167, pp. 225–230 (1988).
J. Clin. Pathol., 44, pp. 115–118 (1991).
J. Clin. Pathol., 42, pp. 840–846 (1989).
Cancer, vol. 62, pp. 73–726 (1988).

*Primary Examiner*—Gary L. Kunz
*Attorney, Agent, or Firm*—Armstrong, Westerman, Hattori, McLeland & Naughton

[57] ABSTRACT

Rapid and easy preparation of a sample for a gene analysis or high-purity nucleic acid suitable for gene amplification especially, for example, by the PCR method is made possible by a process for treating a paraffin-embedded tissue sample to be used for a gene analysis, which comprises heating an aqueous suspension containing a surfactant having a protein-denaturational action and a deparaffinized tissue sample obtained from a paraffin-embedded tissue sample at 60° C. or higher, or the above-mentioned process which further comprises reacting the heat-treated aqueous solution with a protease, or the above-mentioned process which further comprises reacting the heat-treated aqueous solution with a protease, mixing the resulting reaction solution with a solution containing an organic compound having a protein-denaturational action other than the aforesaid surfactant, and precipitating nucleic acid from the resulting reaction solution by addition of an alcohol.

10 Claims, 6 Drawing Sheets

F I G. 4
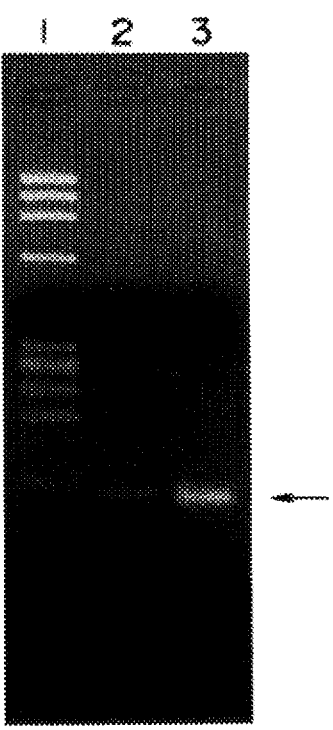

TREATMENT OF PARAFFIN EMBEDDED TISSUE FOR GENE ANALYSIS

BACKGROUND OF THE INVENTION

This invention relates to a process for treating a paraffin-embedded tissue sample useful for a gene analysis, and a treating kit for practicing the process.

In the field of pathology, gene analyses have recently been carried out for diagnoses of genopathies, infectious diseases, malignant tumors, etc. and inspection for gene abnormality responsible for these diseases. In particular, extraction of nucleic acid from a formaldehyde fixed and paraffin embedded tissue was first made possible by Goelz et al. in 1985 (Goelz, S. E. et al.: Biochem. Biophys. Res. Commun., 130: 118–126, 1985). Since it was reported that various molecular biological inspections can be carried out on the basis of the above extraction, gene analyses by the polymerase chain reaction method (PCR method), etc. have been carried out as retrospective inspection on samples whose histopathological background has been elucidated by morphological observation carried out mainly by hematoxylin-eosin (H.E) staining, etc.

As a conventional process for treating a paraffin-embedded tissue sample useful for a gene analysis, such as extraction of nucleic acid, there is generally employed a process which comprises treating tissue cells freed of paraffin with a solution containing a surfactant, a protease, etc. at room temperature to about 50° C. for 4 to 48 hours to disrupt the tissue cells, removing impurities, i.e. substances other than nucleic acid by a two-phase separation method (i.e. a method comprising separation into an aqueous phase containing the nucleic acid and an organic solvent phase containing denatured protein and the like by addition of one or more organic solvents such as phenol, chloroform, etc.), and then adding an alcohol to the residue to precipitate the nucleic acid in the aqueous phase (Jikken Igaku, Vol. 8, No. 9, pp. 84–88, 1990, YODOSHA CO., LTD.).

The above-mentioned process for treating a paraffin-embedded tissue sample useful for a gene analysis, however, is disadvantageous in that since the disruption of the tissue cells freed of paraffin is carried out by simultaneous use of a surfactant and a protease under a relatively mild condition, more specifically, at room temperature to about 50° C., the denaturation and decomposition reaction should be carried out for a long period of time (usually 4 to 48 hours) for increasing the recovery of the nucleic acid. In addition, the removal of the impurities, i.e., the substances other than the nucleic acid by the two-phase separation method using phenol, chloroform, etc. which is carried out after the disruption of the tissue cells freed of paraffin is also disadvantageous in that a long time and much labor are required for the separation between the organic solvent phase and the aqueous phase and that the troublesome operations for the separation cause contamination with adventitious nucleic acid. Furthermore, employment of the nucleic acid obtained by said process as a sample for a gene analysis using the PCR method involves many problems because the nucleic acid have not sufficiently been freed of substances inhibitory to gene amplification carried out by the PCR method.

On the other hand, there is disclosed another process comprising treating a deparaffinized tissue sample in a solution containing a surfactant (e.g. sodium dodecyl sulfate) but not containing a protease, etc., at 37° C. for 15 minutes, adding proteinase K, treating the resulting mixture at 37° C. for 12 hours to disrupt the tissue cells, and adding phenol and chloroform to the resulting solution, followed by conventional procedures [Laboratory Medicine, vol. 22, No. 8,. p 543–546 (1991)]. The treating time of this process is considerably shortened compared with other prior art processes, but still requires 12 hours or longer. Further, since the removal of impurities after the cell disruption treatment is conducted by the above-mentioned two-phase separation method, the procedure is complicated and often causes a problem of insertion of foreign nucleic acid during the complicated procedure. In addition, since inhibitory substances for gene amplification reaction by the PCR method are not sufficiently removed from the resulting nucleic acid, there are still much problems when used as a sample for a gene analysis applying the PCR method.

SUMMARY OF THE INVENTION

The present invention was made in view of such conditions and is intended to provide a process for treating a paraffin-embedded tissue sample useful for a gene analysis, which makes it possible to obtain nucleic acid rapidly and easily; a process for treating a paraffin-embedded tissue sample useful for a gene analysis, which makes it possible to obtain high-purity nucleic acid suitable for gene amplification by the PCR method rapidly and easily; and a kit for practicing any of these processes.

The present invention provides a process for treating a paraffin-embedded tissue sample to be used for a gene analysis, which comprises heating an aqueous suspension containing a deparaffinized tissue sample obtained from a paraffin-embedded tissue sample and a surfactant having a protein-denaturational action at 60° C. or higher.

The present invention also provides a process for treating a paraffin-embedded tissue sample to be used for a gene analysis, which comprises heating an aqueous suspension containing a deparaffinized tissue sample obtained from a paraffin-embedded tissue sample and a surfactant having a protein-denaturational action at 60° C. or higher, and then reacting the heat-treated aqueous suspension with a protease.

In addition, the present invention provides a process for treating a paraffin-embedded tissue sample to be used for a gene analysis, which comprises heating an aqueous suspension containing a deparaffinized tissue sample obtained from a paraffin-embedded tissue sample and a surfactant having a protein-denaturational action, reacting the heat-treated aqueous suspension with a protease, and then precipitating nucleic acid from the resulting reaction solution.

Further, the present invention provides a process for treating a paraffin-embedded tissue sample to be used for a gene analysis, which comprises heating an aqueous suspension containing a deparaffinized tissue sample obtained from a paraffin-embedded tissue sample and a surfactant having a protein-denaturational action, reacting the heat-treated aqueous suspension with a protease, mixing the resulting reaction solution with a solution containing an organic compound having a protein-denaturational action other than the surfactant mentioned above, and then precipitating nucleic acid from the resulting reaction solution.

Still further, the present invention provides a kit for treating a paraffin-embedded tissue sample to be used for a gene analysis, which comprises a container containing a surfactant having a protein-denaturational action, a container containing a protease, and a container containing a hydroxybenzoic acid solution.

BRIEF DESCRIPTION OF THE DRAWINGS

FIG. 4 is a photograph showing the results of 2.5% agarose gel electrophoresis of each DNA sample obtained in Example 4 which was carried out after amplification of the DNA sample by the PCR method.

DESCRIPTION OF THE PREFERRED EMBODIMENTS

Figure 1:
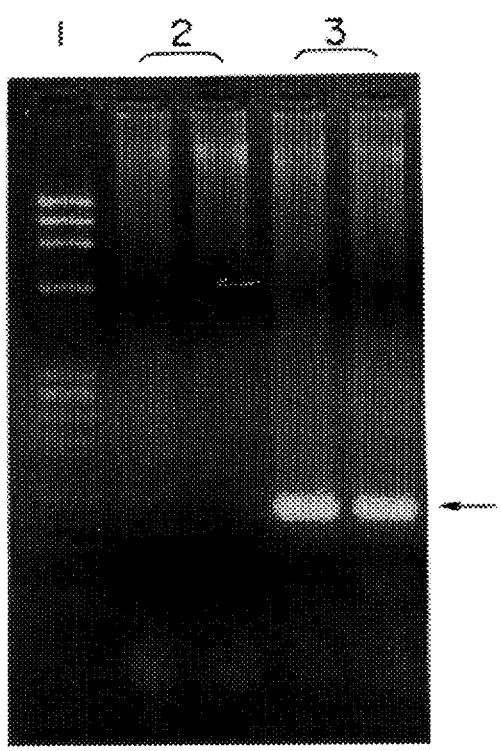
FIG. 1 is a photograph showing the results of 3% agarose gel electrophoresis of DNA sample obtained in each of Example 1 and Comparative Example 1 which was carried out after amplification of the DNA sample by the polymerase chain reaction method (PCR method).

The present inventors earnestly investigated in order to achieve the above objects, and consequently found that in a process for treating a paraffin-embedded tissue sample useful for a gene analysis, either the heat treatment of an aqueous suspension containing a surfactant having a protein-denaturational action and a deparaffinized tissue sample obtained from a paraffin-embedded tissue sample, or the reaction of the heat-treated aqueous suspension with a protease is advantageous because when the heat treatment or the reaction is carried out in stead of the conventional treatment, i.e., the disruption of the deparaffinized tissue cells, i.e. freed of paraffin, which step is carried out by simultaneous use of a surfactant and a protease under relatively mild conditions, the problem in the conventional process, i.e., the requirement of a long period of time for the disruption of the tissue cells is solved, namely, the time required for the disruption can be greatly reduced. In addition, the present inventors found the following. The effects described below can be obtained when a surfactant having a protein-denaturational action is added to a tissue sample after removal of paraffin from a paraffin-embedded tissue, and the resulting aqueous suspension is heated, after which the heat-treated aqueous suspension is reacted with a protease, and a protein denaturation and removal procedure is carried out by an one-phase method by use of a solution containing an organic compound having a protein-denaturational action, for example, an aqueous alcoholic solution containing an organic compound having one or more phenolic hydroxyl groups, instead of carrying out a protein denaturation and removal procedure by the two-phase separation method using phenol, chloroform, etc. as in the conventional process. The effects are as follows. The problems in the conventional process (i.e. the troublesome operations and the high possibility of contamination with foreign nucleic acid, which are attributable to the need for the separation; and the insufficient removal of substances inhibitory to the PCR reaction) are solved, so that simplification of the steps of procedure and reduction of the operation time become possible. Moreover, there can be obtained nucleic acid which are suitable for the PCR method because of their contamination with only a slight amount of substances inhibitory to gene amplification by the PCR method. Thus, the present invention has been accomplished.

As the paraffin-embedded tissue sample used in the present invention, there can be exemplified all of samples containing nucleic acid and usually called "paraffin-embedded tissue sample" in the art, for example, samples prepared by subjecting a collected tissue material (e.g. pancreas, large intestine, cancer of large intestine, muscle, urinary bladder, kidney, lung, brain, lymphoma, etc.) to fixing treatment with a liquid chemical having a protein-coagulative action (e.g. a formaldehyde solution, glutaraldehyde solution, formaldehyde-alcohol mixed solution, alcohol solution, Bouin solution, Zenker solution, Hely solution, osmic acid solution, Carnoy solution, etc.) in order to keep the fine structure of tissue cells and carry out a pretreatment for sample preparation, and embedding the thus treated tissue material in paraffin.

For removing paraffin from the paraffin-embedded tissue sample used in the present invention, any method may be used so long as it is usually employed in the art for removing paraffin from a paraffin-embedded tissue sample. There can be exemplified a method comprising adding a water-insoluble organic solvent to the paraffin-embedded tissue sample, stirring and shaking the resulting mixture, centrifuging the mixture, and discarding the supernatant to remove paraffin. The water-insoluble organic solvent for dissolving and removing the paraffin which is used in such a method is not particularly limited, and any water-insoluble organic solvent may be used so long as it is usually used in the art for dissolving and removing paraffin. Preferable example of the water-insoluble organic solvent are xylene, D-limonene, octane, etc. Of these, D-limonene and the like are preferable in view of toxicity to a human body. Although the amount of the water-insoluble organic solvent used cannot be unequivocally determined because it is varied depending on the thickness of the tissue sample, etc., it may be an amount sufficient to immerse the tissue sample therein thoroughly.

The surfactant used in the present invention is not particularly limited and may be any of cationic surfactants, anionic surfactants, nonionic surfactants and amphoteric surfactants so long as it is usually used in the art as an surfactant having a protein-denaturational action. Typical and specific examples of the surfactant are cationic surfactants such as dodecyltrimethylammonium bromide, dodecyltrimethylammonium chloride, cetyltrimethylammonium bromide and the like; anionic surfactants such as sodium dodecylsulfate (SDS), sodium N-lauroylsarcosine, sodium cholate, sodium deoxycholate and the like; nonionic surfactants such as polyoxyethylene octylphenyl ether [e.g. Triton X-100 (a trademark, Rohm and Haas Co.), etc.], polyoxyethylene sorbitan monolaurate [e.g. TWEEN 20 (a trademark, Kao Corp.), etc.], polyoxyethylene sorbitan monooleate [e.g. TWEEN 80 (a trademark, Kao Corp.), etc.], n-octyl-β-D-glucoside and the like; and amphoteric surfactants such as 3-[(cholamidopropyl)-dimethylammonio]-1-propane sulfonate, phosphatidylethanolamine and the like. Of these surfactants, the anionic surfactants such as SDS are particularly preferable because of their strong protein-denaturational action. The above-exemplified surfactants can be used singly or as a mixture thereof.

One of the processes for treating a paraffin-embedded tissue sample useful for a gene analysis of the present invention can be practiced by preparing an aqueous suspension containing the above-mentioned deparaffinized tissue sample obtained from the paraffin-embedded tissue sample and the above-mentioned surfactant having a protein-denaturational action, and heating the aqueous suspension.

A method for preparing the aqueous suspension containing deparaffinized tissue sample obtained from the paraffin-embedded tissue sample and the surfactant having a protein-denaturational action is not particularly limited and any method may be employed so long as it finally gives the aqueous suspension containing deparaffinized tissue sample obtained from the paraffin-embedded tissue sample and the surfactant having a protein-denaturational action. A preferable example of the most general method for the preparation is a method of adding an aqueous solution containing the surfactant having a protein-denaturational action to the deparaffinized tissue sample obtained from the paraffin-embedded tissue sample, to suspend the deparaffinized tissue sample.

The concentration of the surfactant used in the present invention is varied a little depending on the kind of the surfactant, though for example, the concentration in the aqueous solution containing the surfactant having a protein-denaturational action is usually 0.01 to 10% (W/V), preferably 0.1 to 2% (W/V).

The aqueous suspension containing the deparaffinized tissue sample obtained from the paraffin-embedded tissue sample and the surfactant having a protein-denaturational action may contain, for example, buffers such as phosphate buffers, citrate buffers, tris(hydroxymethyl)aminomethane (Tris) buffer, glycine buffer, Good's buffers, etc. and salts such as sodium chloride, potassium chloride, magnesium chloride, lithium chloride, etc. In addition, the aqueous suspension may, if necessary, properly contain nuclease inhibitors such as ethylenediaminetetraacetic acid (EDTA), ethylene glycol bis(2-aminoethyl ether) tetraacetic acid (EGTA), salts thereof, etc. Needless to say, when the surfactant having a protein-denaturational action has also nuclease-inhibitory action, the above-exemplified nuclease inhibitors need not be used. The concentrations of the buffers, salts and nuclease inhibitors used are not critical so long as they do not hinder the liberation of nucleic acid. For example, the concentration of the buffers in the aqueous solution containing the surfactant having a protein-denaturational action is usually 1 to 500 mM, preferably 5 to 200 mM. The salts are added to a concentration of 1 to 500 mM if necessary. Although the pH of the aqueous solution is not critical so long as it does not hinder the liberation of nucleic acid, it is properly chosen in the range of usually 2 to 12, preferably 5 to 9. The concentration of the nuclease inhibitors used cannot be unequivocally determined because it is varied depending on the kind of the inhibitor. For example, when EDTA is used, the concentration of EDTA in the aqueous solution is usually 0.1 to 200 mM, preferably 1 to 10 mM.

The heating conditions in the treating process of the present invention are as follows. The heating temperature is usually 60° C. or higher, preferably 70° C. or higher, preferably to a temperature of the boiling point of the suspension or lower, more preferably 80° C. to the boiling point of the suspension. As the heating time, usually 2 minutes or more, preferably 5 to 30 minutes, is sufficient.

Needless to say, the boiling point of the suspension changes to a certain extent with a change of the external pressure and changes of the proportions and concentrations of the substances contained in the suspension.

The treating process of the present invention is more concretely described, for example, as follows.

A slice (thickness: usually about 10 μm) of a paraffin-embedded tissue is placed in a test tube, and a proper amount (an amount sufficient to immerse the tissue slice) of a water-insoluble organic solvent such as xylene, limonene, etc. is added. After sufficient stirring and shaking, the resulting mixture is centrifuged at ordinary temperature and the supernatant is discarded to remove the paraffin. The above procedure is repeated once on the precipitate. Then, a proper amount of a volatile organic solvent such as ethanol is added to the thus obtained precipitate, and after stirring and shaking, the resulting mixture is centrifuged at ordinary temperature and the supernatant is discarded to remove the water-insoluble organic solvent. This procedure is repeated once on the precipitate. The thus obtained pellet is dried. Subsequently, the dried pellet is suspended in an aqueous solution containing 0.01 to 10% (W/V) of the surfactant having a protein-denaturational action, and the resulting suspension is heated at 70° C. or higher for 2 minutes or more. Thus, the treating process of the present invention can be practiced.

The sample for a gene analysis obtained by the treatment by the above-mentioned process (hereinafter referred to as "sample A for gene analysis") can be used as it is as a sample for a gene analysis by the PCR method, or the like., or it can be used as a sample from which nucleic acid are extracted and purified by a method usually used in the art.

A sample useful for a gene analysis by the PCR method, or the like, can be prepared also by treating a paraffin-embedded tissue sample for a gene analysis by practicing the above-mentioned treating process (i.e. heating the aqueous suspension containing a surfactant having a protein-denaturational action and a deparaffinized tissue sample obtained from a paraffin-embedded tissue sample), and then reacting the heat-treated aqueous suspension with a protease. Such a process permits simplification of the steps of procedure and hence marked reduction of the operation time as compared with conventional processes. Furthermore, the treatment with a protease is effective, for example, in that the efficiency of extraction of nucleic acid from the paraffin-embedded tissue sample is further increased.

The protease used in the present invention is not particularly limited so long as it is usually used in the art for the purpose of digesting a protein. Preferable examples of the protease are papain, proteinase K, pronase, etc. As to the concentration of the protease used, the concentration in the reaction mixture in the protein digestion step is usually 0.01 to 10 mg/ml.

When there is used a protease thermostable (heat-resistant) even at a high temperature of, for example, 70° C. or higher which has catalytic activity under the heating conditions employed in the present invention, the protease can be allowed to act simultaneously with the heat treatment of the aqueous suspension containing the deparaffinized tissue sample obtained from the paraffin-embedded tissue sample and the surfactant having a protein-denaturational action which is carried out in the present invention. Thus, the steps of procedure can be further simplified.

The above-mentioned process for treating a paraffin-embedded tissue sample useful for a gene analysis is practiced, for example, as follows.

To the sample A for gene analysis obtained by the treatment by the above-mentioned treating process (i.e. the sample obtained by heating the aqueous suspension containing the deparaffinized tissue sample obtained from the paraffin-embedded tissue sample and the surfactant having a protein-denaturational action, under the above-mentioned conditions) is added the protease in an amount of 0.01 to 10 mg/ml, and the reaction is carried out at 37–70° C., preferably 40°–60° C. for 5 to 300 minutes. Thus, said process can be practiced. At the time of addition of the protease, a thiol compound [e.g. dithiothreitol (DTT)], i.e., an activator for the protease may be optionally added. Particularly when papain is used as the protease, the thiol compound is preferably added.

The sample for a gene analysis obtained by the process described above (hereinafter referred to as "sample B for gene analysis") can be used as it is as a sample for a gene analysis by the PCR method, or the like, or it can be used as a sample from which nucleic acid are extracted and purified by a method usually used in the art.

In detail, a sample useful for a gene analysis by the PCR method, or the like, can be prepared by practicing the above-mentioned process for treating a paraffin-embedded tissue sample for a gene analysis (i.e. heating the aqueous suspension containing a surfactant having a protein-denaturational action and a deparaffinized tissue sample obtained from a paraffin-embedded tissue sample and reacting the heat-treated aqueous suspension with a protease), followed by precipitating and collecting nucleic acid from the resulting reaction solution. When the paraffin-embedded tissue sample to be used for a gene analysis is thus treated, simplification of the steps of procedure and hence marked reduction of the operation time can be achieved as compared with conventional processes.

A precipitant used for precipitating nucleic acid in the present invention is not particularly limited so long as it is usually used in the art for precipitating nucleic acid. For example, alcohols are used as the precipitant. The alcohols are not particularly limited so long as they are usually used in the art for precipitating nucleic acid. Preferable examples of the alcohols are ethanol, isopropanol, etc. For precipitating desired nucleic acid, the alcohol is used usually in a volume of 0.5 to 3 times that of a solution containing the extracted nucleic acid.

The above process for treating a paraffin-embedded tissue sample using for a gene analysis is practiced, for example, as follows.

The alcohol is added to the sample B for gene analysis obtained by the treatment by the treating process described above (i.e. the sample obtained by heating the aqueous suspension containing the deparaffinized tissue sample obtained from the paraffin-embedded tissue sample and the surfactant having a protein-denaturational action, and reacting the heat-treated aqueous suspension with a protease) in a volume of 0.5 to 3 times that of the sample B for gene analysis and mixed therewith, after which the resulting mixture is allowed to stand at room temperature for 10 minutes. For facilitating the precipitation of nucleic acid, a proper amount of a salt such as NaCl, sodium acetate or the like may be optionally added together with the alcohol. After the standing, the mixture is centrifuged to precipitate the nucleic acid and the supernatant is discarded, and a proper volume of, for example, 70% ethanol is added to the precipitate, followed by washing and centrifugation. The supernatant is discarded and the thus obtained precipitate is dried, whereby there can be obtained a desired sample for a gene analysis (hereinafter referred to as "sample C for gene analysis").

When the sample C for gene analysis is used as a sample for a gene analysis by the PCR method, or the like, it is preferable to use purified DNA obtained by treating the sample C for gene analysis by a method usually employed in the art, for example, a method comprising redissolving the sample C for gene analysis in TE buffer (10 mM Tris-HCl buffer, containing 1 mM EDTA, pH 8.0), adding a suitable amount of RNase, and incubating the resulting solution at 37°–55° C. for 1 to 90 minutes to digest RNA.

The effects described below can be obtained when a paraffin-embedded tissue sample to be used for a gene analysis is treated by practicing the above-mentioned process (i.e. heating the aqueous suspension containing a surfactant having a protein-denaturational action and a deparaffinized tissue sample obtained from a paraffin-embedded tissue sample, and reacting the heat-treated aqueous suspension with a protease), mixing the resulting reaction solution with a solution containing an organic compound having a protein-denaturational action other than the surfactant mentioned above, and then precipitating and collecting nucleic acid from the resulting reaction solution. The effects are as follows. Simplification of the steps of procedure and hence marked reduction of the operation time can be achieved as compared with conventional processes. Furthermore, there can be collected nucleic acid which are suitable for the PCR method because of their contamination with only a slight amount of substances inhibitory to gene amplification by the PCR method.

The aforesaid organic compound having a protein-denaturational action other than the surfactant mentioned above which is used in the present invention is not particularly limited so long as it has the aforesaid action and is water-soluble to a certain extent. Preferable examples of the organic substance are organic compounds having one or more phenolic hydroxyl groups. Specific examples of the organic compounds having one or more phenolic hydroxyl groups are phenol, o-, m- or p-hydroxybenzoic acid, 2-amino-4-chlorophenol, m-aminophenol, methyl p-hydroxybenzoate, catechol, guaiacol, hydroquinone, p-hydroxyphenethyl alcohol, protocatechuic acid, p-(methoxyethyl)phenol, etc. Of these, compounds not corrosive to human skin, such as hydroxybenzoic acid, in particular, m-hydroxy-benzoic acid are preferable. Although the using concentration of the organic compound having one or more phenolic hydroxyl groups is varied depending on the kind of the compound, the concentration of the compound in the reaction solution in the protein denaturation step is usually less than 20% (W/V) and not less than 0.01% (W/V). When m-hydroxybenzoic acid is used, its concentration in said reaction solution is preferably 1 to 10% (W/V).

The solution containing the organic compound used for denaturing protein in the present invention is not critical so long as it is a solution containing the above-exemplified organic compound having a protein-denaturational action. Said solution may contain water-soluble organic solvents such as alcohols (e.g. ethanol, isopropanol, etc.), acetone and the like for the dissolution of said organic compound. Of these organic solvents, the alcohols such as ethanol, isopropanol, etc. are preferable because they have no undesirable influence on the precipitation of nucleic acid. The organic solvents are properly used so that their concentration in said solution may be usually 10 to 90% (W/V). Although the pH of the solution containing said organic compound cannot be unequivocally determined because it is varied depending on the kind of the organic compound, any pH may be employed so long as it does not hinder the protein denaturation. Usually, the pH is properly chosen in the range of 4 to 10. When m-hydroxybenzoic acid is used as the organic compound, the pH of said solution is chosen in the range of 5 to 8. Needless to say, in every case, the organic compound should be in a uniformly dissolved state in said solution.

The above process for treating a paraffin-embedded tissue sample to be used for a gene analysis is practiced, for example, as follows.

The solution containing the organic compound having a protein-denaturational action is added to the sample B for gene analysis obtained by the treatment by the treating process described above (i.e. the sample obtained by heating the aqueous suspension containing the deparaffinized tissue sample obtained from the paraffin-embedded tissue sample and the surfactant having a protein-denaturational action, and reacting the heat-treated aqueous suspension with a protease). Then, the reaction is carried out at room temperature for several minutes to several hours to denature protein, after which the resulting reaction solution is centrifuged and the supernatant is transferred into another tube. Thereafter, an alcohol is added to the supernatant in a volume of 0.5 to 3 times that of the supernatant and mixed therewith, after which the resulting mixture is allowed to stand at room temperature for 10 minutes. In this case, for facilitating the precipitation of nucleic acid, a proper amount of a salt such as NaCl, sodium acetate or the like may be optionally added together with the alcohol. After the standing, the mixture is centrifuged to precipitate the nucleic acid and the supernatant is discarded, and a proper volume of, for example, 70% ethanol is added to the precipitate, followed by washing and centrifugation. The supernatant is discarded and the thus obtained precipitate is dried, whereby there can be obtained a desired sample for a gene analysis (hereinafter referred to as "sample D for gene analysis").

When the sample D for gene analysis is used as a sample for a gene analysis by the PCR method, or the like, it is preferable to use purified DNA obtained by treating the sample D for gene analysis by a method usually employed in the art, for example, a method comprising redissolving the sample D for gene analysis in TE buffer (10 mM Tris-HCl buffer, containing 1 mM EDTA, pH 8.0), adding a suitable amount of RNase, and incubating the resulting solution at 37°–55° C. for 1 to 90 minutes to digest RNA.

The kit for treating a paraffin-embedded tissue sample using for a gene analysis of the present invention is used for practicing any of the above-mentioned processes for treating a paraffin-embedded tissue sample to be used for a gene analysis, and comprises a container containing a surfactant having a protein-denaturational action, a container containing a protease, and a container containing a hydroxybenzoic acid solution. Preferable properties, specific examples and the like of each of the components contained in the containers are as described above.

The present invention is explained below in further detail with reference to Examples, Comparative Examples and Reference Examples, which are not by way of limitation but by way of illustration.

EXAMPLE 1

DNA extraction method using m-hydroxybenzoic acid

A slice of formaldehyde fixed and paraffin embedded human tissue (liver, thickness 10 µm, about 15 mm×25 mm) was placed in a 1.5-ml test tube, followed by adding thereto 1 ml of D-limonene (Lemosol, a trade name, mfd. by Wako Pure Chemical Industries, Ltd.), and the resulting mixture was stirred with a micro-tube mixer (MT-360, mfd. by Tomy Seiko Co., Ltd.) for 3 minutes. The mixture was then centrifuged at 12,000 rpm for 3 minutes at ordinary temperature, and the supernatant was discarded to remove the paraffin. The above procedure was repeated once on the precipitate. Subsequently, 1 ml of ethanol was added to the thus obtained precipitate and the resulting mixture was stirred with the aforesaid mixer and then centrifuged at 12,000 for 3 minutes at ordinary temperature, after which the supernatant was discarded to remove a slight amount of the remaining D-limonene. This procedure was repeated once on the precipitate, and the thus obtained pellet was dried. To the dried pellet was added 180 µl of 11 mM Tris-HCl buffer (pH 7.0, containing 1.11% SDS and 5.6 mM EDTA), and the resulting suspension was heated at 90° C. for 10 minutes. Then, 20 µl of 1M DTT and 10 µl of a 20 mg/ml papain solution were added to the heated suspension, after which the reaction was carried out at 50° C. for 90 minutes. Thereafter, 200 µl of a 40% (V/V) aqueous isopropanol solution (pH 6.0) containing 10% (W/V) m-hydroxybenzoic acid was added to the reaction solution, and the resulting mixture was subjected to reaction at room temperature for 30 minutes. The thus obtained reaction solution was centrifuged at 12,000 rpm for 5 minutes and the supernatant was transferred into another tube by decantation. With the supernatant were mixed 40 µl of a 3M aqueous NaCl solution and 900 µl of isopropanol, and the resulting mixture was allowed to stand at room temperature for 10 minutes and then centrifuged at 12,000 rpm for 15 minutes to precipitate nucleic acid. The supernatant was discarded and 1 ml of 70% ethanol was added to the precipitate and stirred, after which the resulting mixture was centrifuged at 15,000 rpm for 5 minutes at 4° C. Then, the supernatant was discarded and the precipitate was dried to obtain the desired nucleic acid. Finally, the obtained nucleic acid were redissolved in 20 µl of TE buffer (10 mM Tris-HCl buffer, containing 1 mM EDTA, pH 8.0), followed by adding thereto 1 µl of 10 mg/ml RNase, and the resulting solution was incubated at 50° C. for 1 hour to obtain a DNA sample. The DNA yield in the DNA sample was determined by fluorometry and the β-globin gene was amplified by the PCR method by use of the DNA sample (conditions in the PCR method: 94° C. for 1 minute, 55° C. for 2 minutes, 72° C. for 3 minutes; 35 cycles). The DNA quantitation by fluorometry was carried out by the following method.

To 1 µl of the obtained DNA sample was added 10 µl of 2M 3,5-diaminobenzoic acid-2HCl, and stirred, after which the reaction was carried out at 60° C. for 30 minutes. Then, 1 ml of a 0.6 N perchloric acid solution was added to the reaction solution and the fluorescence intensity (Ex=415 nm, Em=515 nm) was measured by means of a fluorescence detector. The amount of DNA in the DNA sample was calculated using a calibration curve obtained on the basis of measurement results obtained for DNA standard samples prepared from DNA of a known concentration.

Table 1 shows the DNA yield in the DNA sample, etc., and FIG. 1 (lane 3) shows the result of fluorometric detection of DNA carried out by means of a UV illuminator after electrophoresis of the DNA amplified by the PCR method, at a constant voltage of 100 V for 20 to 30 minutes on a 3% agarose gel prepared by use of 1×TAE buffer (0.04M Tris-acetate, 1 mM EDTA, pH 7.8) containing 0.5 µg/ml of ethidium bromide. In FIG. 1, lane 1 shows the result obtained for a molecular weight marker (φ×174 phage DNA/HaeIII, mfd. by Nippon Gene Co., Ltd.). The mark ← indicates the amplification region (110 bp) of the human β-globin gene.

Comparative Example 1

DNA extraction by a known method (a method using phenol)

A slice of formaldehyde fixed and paraffin embedded human tissue (liver, thickness 10 µm, about 15 mm×25 mm) was placed in a 1.5-ml test tube, followed by adding thereto 1 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at room temperature, and the supernatant was discarded to remove the paraffin. The above procedure was repeated once on the precipitate. Subsequently, 1 ml of ethanol was added to the thus obtained precipitate and the resulting mixture was stirred with the aforesaid mixer and then centrifuged at 12,000 for 3 minutes at room temperature, after which the supernatant was discarded to remove a slight amount of the remaining D-limonene. This procedure was repeated once on the precipitate, and the thus obtained pellet was dried. To the dried pellet was added 300 μl of SSC buffer (containing 0.15M sodium chloride and 0.015M sodium acetate, pH 7.0) containing 1% SDS and 0.1 mg/ml proteinase K (or papain), after which the reaction was carried out at 48° C. for 48 hours. In the course of the reaction, 50 μl of a 1 mg/ml proteinase K solution (or a 1 mg/ml papain solution) was added three times. The reaction solution was mixed with an equal volume of a phenol/chloroform/isoamyl alcohol mixture (25:24:1), and the resulting mixture was centrifuged at 6,000 rmp for 5 minutes, after which the aqueous phase, the upper layer was transferred into another tube by pipetting. This separating procedure was repeated once on the aqueous layer. The thus obtained aqueous phase was mixed with an equal volume of a chloroform/isoamyl alcohol mixture (24:1), and the resulting mixture was centrifuged at 6,000 rmp for 5 minutes, after which the upper layer was transferred into another tube. This procedure was repeated once. A 5M sodium chloride solution and ethanol were added to the obtained upper layer solution in volumes of three-fiftieths and 2.5 times, respectively, as large as the upper layer solution and stirred, after which the resulting mixture was allowed to stand at −80° C. for 15 minutes. Then, the mixture was centrifuged at 15,000 rpm for 20 minutes at 4° C. and the supernatant was discarded. The pellet was mixed with 70% ethanol and the resulting mixture was centrifuged at 15,000 rpm for 5 minutes at 4° C., after which the supernatant was discarded and the precipitate was dried to obtain desired nucleic acid. Finally, the obtained nucleic acid were redissolved in 20 μl of TE buffer, followed by adding thereto 1 μl of 10 mg/ml RNase, and the resulting solution was incubated at 50° C. for 1 hour to obtain a DNA sample. The DNA yield in the DNA sample was determined by fluorometry and the β-globin gene was amplified by the PCR method by use of the DNA sample under the same conditions as described in Example 1. The DNA quantitation by fluorometry was carried out by the following method.

To 1 μl of the obtained DNA sample was added 10 μl of 2M 3,5-diaminobenzoic acid-2HCl, and stirred, after which the reaction was carried out at 60° C. for 30 minutes. Then, 1 ml of a 0.6 N perchloric acid solution was added to the reaction solution and the fluorescence intensity (Ex=415 nm, Em=515 nm) was measured by means of a fluorescence detector. The amount of DNA in the DNA sample was calculated using a calibration curve obtained on the basis of measurement results obtained for DNA standard samples prepared from DNA of a known concentration.

Table 1 shows the DNA yield in the DNA sample, etc. together with the results obtained in Example 1, and FIG. 1 (lane 2) shows the result of fluorescence detection for DNA carried out by means of a UV illuminator after electrophoresis of the DNA amplified by the PCR method, at a constant voltage of 100 V for 20 to 30 minutes on a 3% agarose gel prepared by use of 1×TAE buffer (0.04M Tris-acetate, 1 mM EDTA, pH 7.8) containing 0.5 μg/ml of ethidium bromide, together with the results obtained in Example 1.

TABLE 1

|  | Example 1 | Comparative Example 1 |
|---|---|---|
| Total operation time | 3 hours | 3 days |
| Protein removal by two-phase method | None | Carried out |
| DNA yield (μg/slice) | 3.2 | 3.1 |

As is clear from the results shown in Table 1, when process of the present invention (Example 1) and the known method (Comparative Example 1) are compared for the total operation time required for attaining the same DNA yield, the total operation time is much shorter in the process of the present invention than in the known method. This result is due to various factors and main factors are as follows. In the known method, since the protein denaturation and digestion is carried out by simultaneous use of a surfactant and a protease, it is necessary to carry out this reaction for a long period of time (48 hours) for increasing the recovery of nucleic acid, and then carry out the step of protein denaturation and removal by the two-phase separation method using phenol, chloroform, etc. By contrast, the process of the present invention permits rapid extraction of nucleic acid in substantially the same yield as in the known method because the same procedure as in the known method is carried out by the steps of the heat treatment for protein denaturation by use of a surfactant, the protein digestion by use of a protease, and then the protein denaturation and removal by an one-phase method using a solution containing an organic compound having a protein-denaturational action.

In addition, as is clear from the results shown in Table 1 and FIG. 1, there was no difference of DNA yield when there were compared the result obtained by the process of the present invention and that obtained by the known method. But when each obtained DNA was amplified by the PCR method, amplified fragments of the β-globin gene were observed in the case of the DNA extracted by the process of the present invention but not in the case of the DNA extracted by the known method. This fact indicates that the DNA extracted by the process of the present invention is more suitable for a gene analysis by the PCR method than the DNA extracted by the known method.

Referential Example 1

Detection of PCR-inhibitory substances in the DNA samples obtained in Example 1 and Comparative Example 1

To 13 μl of each of the DNA samples obtained in Example 1 and Comparative Example 1 was added 70 U of DNase, and the reaction was carried out at 37° C. for 1 hour to digest the human DNA. The reaction solution was mixed with an equal volume of a phenol/chloroform/isoamyl alcohol mixture (25: 24: 1) and the resulting mixture was centrifuged at 6,000 rpm for 5 minutes, after which the aqueous layer, the upper layer was transferred into another tube, whereby the DNase was removed. A 5M sodium chloride solution and ethanol were added to the obtained aqueous phase in volumes of three-fiftieths and 2.5 times, respectively, as large as the aqueous phase and stirred, after which the resulting mixture was allowed to stand at −80° C. for 15 minutes. Then, the mixture was centrifuged at 15,000 rpm for 20 minutes at 4° C. and the supernatant was discarded. To the pellet was added 1 ml of 70% ethanol, followed by washing and drying. The resulting pellet was dissolved in 13 μl of TE buffer. The thus obtained solutions were used as sample solutions for the following test.

With 100 attomoles of rat cDNA was mixed 2, 4 or 7 μl of each sample solution, and the rat glucose-3-phosphate dehydrogenase (G3PDH) gene (983 bp region) was amplified by the PCR method (conditions: 94° C. for 45 seconds, 60° C. for 45 seconds, 72° C. for 2 minutes; 30 cycles). Then, the amplified DNA was electrophoresed at a constant voltage of 100 V for 20 to 30 minutes on a 3% agarose gel prepared by use of 1×TAE buffer (0.04M Tris-acetate, 1 mM EDTA, p 7.8) containing 0.5 µg/ml of ethidium bromide. Thereafter, fluorometric detection of objective bands was carried out by means of a UV illuminator. The results obtained are shown in FIG. 2.

Each lane number in FIG. 2 indicates that the result shown in the lane was obtained when the specimen described below was used:

lanes 1 and 6: molecular weight marker (φ×174 phage DNA/HaeIII), lane 2: no sample solution prepared from the DNA sample obtained in Comparative Example 1 was added, lane 3: 2 µl of the sample solution prepared from the DNA sample obtained in Comparative Example 1 was added, lane 4: 4 µl of the sample solution prepared from the DNA sample obtained in Comparative Example 1 was added, lane 5: 7 µl of the sample solution prepared from the DNA sample obtained in Comparative Example 1 was added, lane 7: no sample solution prepared from the DNA sample obtained in Example 1 was added, lane 8: 2 µl of the sample solution prepared from the DNA sample obtained in Example 1 was added, lane 9: 4 µl of the sample solution prepared from the DNA sample obtained in Example 1 was added, lane 10: 7 µl of the sample solution prepared from the DNA sample obtained in Example 1 was added.

Figure 2:
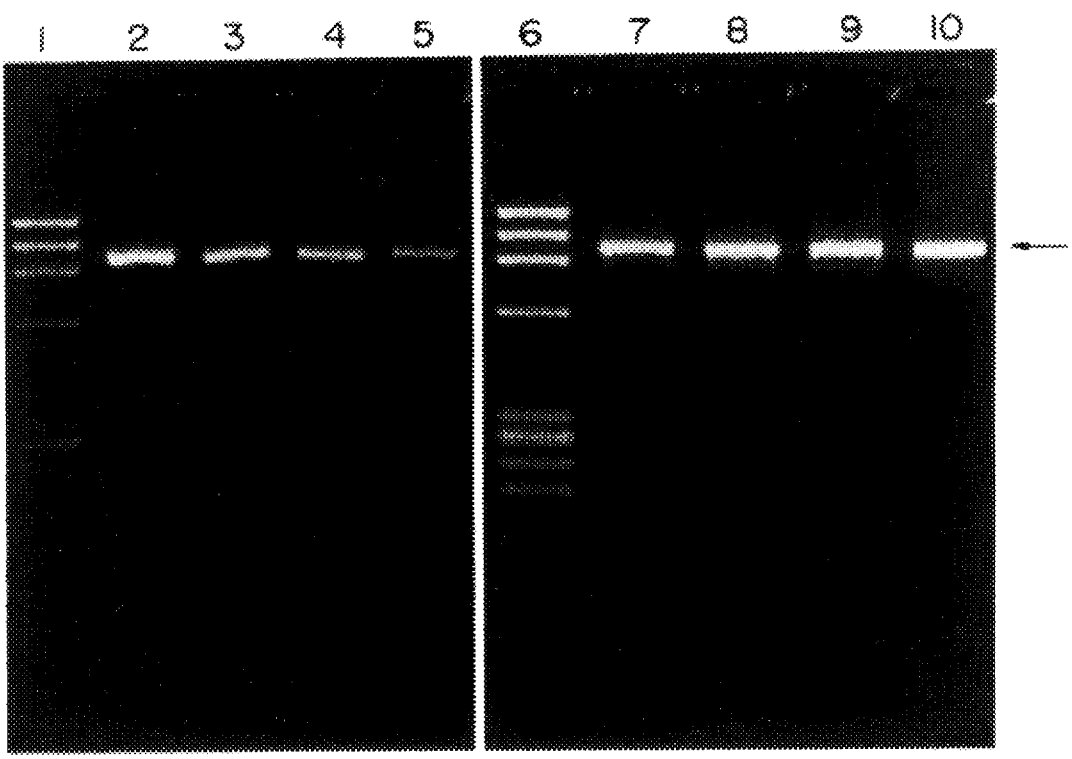
FIG. 2 is a photograph showing the results of 3% agarose gel electrophoresis of rat cDNA carried out after amplification of the cDNA by the PCR method, which were obtained in Referential Example 1.

In FIG. 2, the mark ← indicates the amplification region (983 bp) of the rat G3PDH gene.

From the results shown in FIG. 2, it can be seen that no quantitative change of the amplification band of the rat gene is observed in the case of the specimens containing the sample solution prepared from the DNA sample obtained in Example 1, but that in the case of the specimens containing the sample solution prepared from the DNA sample obtained in Comparative Example 1, the amplification rate of the rat gene tends to be decreased (the width of the amplification band tends to be decreased) with an increase of the adding volume of the sample solution. This fact indicates that the detection of no desired gene after the amplification by the PCR method of the DNA obtained in Comparative Example 1 is attributable to reaction-inhibitory substances harmful to the PCR method which are present in the DNA as contaminants. Therefore, it is judged that the reaction-inhibitory substances harmful to the PCR method cannot be sufficiently removed by the known treating method (Comparative Example 1). On the other hand, it can be seen that according to the treating process of the present invention, nucleic acid suitable for use as a sample in the PCR method can be obtained with substantially no contamination with the substances inhibitory to the reaction carried out in the PCR method.

EXAMPLE 2

DNA extraction from a paraffin-embedded tissue sample by heat treatment

Four tissue slices (thickness 10 µm, about 10mm×20 mm) were cut out of a formaldehyde fixed and paraffin embedded tissue sample (rat liver). Each tissue slice was placed in a 1.5-ml test tube, followed by adding thereto 1 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at room temperature, and the supernatant was discarded to remove the paraffin. The above procedure was repeated once on the precipitate. Subsequently, 1 ml of ethanol was placed in each test tube and the resulting mixture was stirred with the aforesaid mixer and then centrifuged at 12,000 for 3 minutes at ordinary temperature, after which the supernatant was discarded to remove a slight amount of the remaining D-limonene. This procedure was repeated once on the precipitate, and the thus obtained pellet was dried. Then, 180 µl of 11 mM Tris-HCl buffer (pH 7.0, containing 1.11% SDS and 5.6 mM EDTA) was placed in each test tube, and three of the four test tubes were heated at 100° C. for 3 minutes, 5 minutes or 10 minutes, respectively. Thereafter, 20 µl of 1M DTT and 10 µl of a 20 mg/ml papain solution were placed in each of the three test tubes, and the reaction was carried out at 50° C. for 90 minutes. In the remaining test tube were placed 20 µl of 1M DTT and 10 µl of a 20 mg/ml papain solution without heating the test tube, after which the reaction was carried out at 50° C. for 90 minutes. After completion of the reaction in each test tube, 20 µl of TE buffer (10 mM Tris-HCl buffer, containing 1 mM EDTA, p 8.0) was added to each test tube, whereby desired DNA sample solutions were obtained. After 40 µl of each DNA sample solution was electrophoresed at a constant voltage of 100 V for 20 to 30 minutes on a 1% agarose gel prepared by use of 1×TAE buffer (0.04M Tris-acetate, 1 mM EDTA, pH 7.8) containing 0.5 µg/ml of ethidium bromide, fluorometric detection of desired bands was carried out by means of a UV illuminator, whereby the free state of DNA was checked.

Each lane number in FIG. 3 indicates that the result shown in the lane was obtained when the sample described below was used:

lane 1: molecular weight marker (λ phase DNA/HindIII, mfd. by Nippon Gene Co., Ltd.), 2: no heat treatment, 3: heated at 100° C. for 3 minutes, 4: heated at 100° C. for 5 minutes, 5: heated at 100° C. for 10 minutes.

Figure 3:
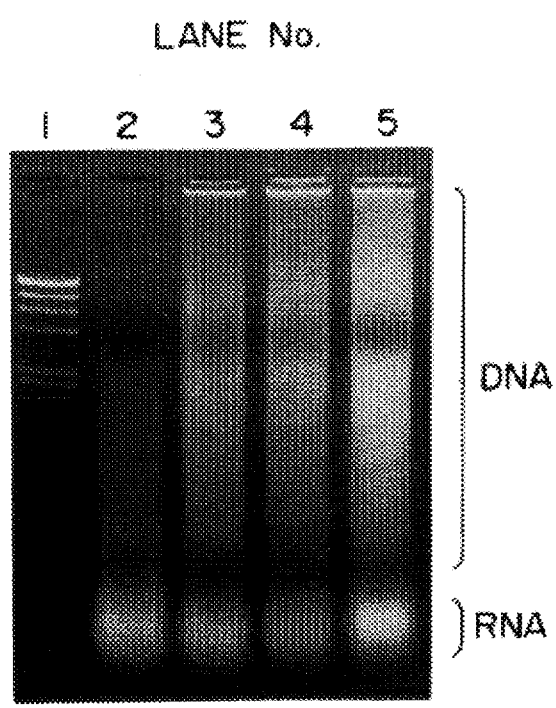
FIG. 3 is a photograph showing the results of 3% agarose gel electrophoresis of each DNA sample obtained in Example 2.

As is clear from the results shown in FIG. 3, when no heat treatment was carried out (lane 2), substantially no fluorescence was observed in the DNA region, namely, the amount of DNA liberated from the tissue was very small. From the results in the case of lanes 3 to 5, it can be seen that the amount of DNA liberated from the tissue was markedly increased by each heat treatment and was increased with an increase of the heating time.

EXAMPLE 3

DNA extraction from a paraffin-embedded tissue sample by heat treatment

Eleven tissue slices (thickness 10 µm, about 10 mm×20 mm) were cut out of a Carnoy fixed and paraffin embedded human tissue sample (liver). Each tissue slice was placed in a 1.5-ml test tube, followed by adding thereto 1 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at ordinary temperature, and the supernatant was discarded to remove the paraffin. The above procedure was repeated once on the precipitate. Subsequently, 1 ml of ethanol was placed in each test tube and the resulting mixture was stirred with the aforesaid mixer and then centrifuged at 12,000 for 3 minutes at ordinary temperature, after which the supernatant was discarded to remove a slight amount of the remaining D-limonene. This procedure was repeated once on the precipitate, and the thus obtained pellet was dried. Then, 180 µl of 11 mM Tris-HCl buffer (pH 7.0, containing 1.11% SDS and 5.6 mM EDTA) was placed in each test tube, followed by heat treatment at a predetermined temperature for a predetermined time. Thereafter, 20 µl of 1M DTT and 10 µl of a 20 mg/ml papain solution were placed in each test tube and the reaction was carried out at 50° C. for 90 minutes. Subsequently, 200 µl of a 40% (V/V) aqueous isopropanol solution (pH 6.0) containing 10% (W/V) m-hydroxybenzoic acid was added to the reaction solution, and the resulting solution was subjected to reaction at room temperature for 30 minutes. The thus obtained reaction solution was centrifuged at 12,000 rpm for 5 minutes and the supernatant was transferred into another tube by decantation. With the supernatant were mixed 40 µl of a 3M aqueous NaCl solution and 900 µl of isopropanol, and the resulting mixture was allowed to stand at room temperature for 10 minutes and centrifuged at 12,000 rpm for 15 minutes to precipitate nucleic acid. The supernatant was discarded and 1 ml of 70% ethanol was added to the precipitate and stirred, after which the resulting mixture was centrifuged at 15,000 rpm for 5 minutes at 4° C. Then, the supernatant was discarded and the precipitate was dried to obtain the desired nucleic acid. Finally, the obtained nucleic acid were redissolved in 20 µl of TE buffer (10 mM Tris-HCl buffer, containing 1 mM EDTA, pH 8.0), followed by adding thereto 1 µl of 10 mg/ml RNase, and the resulting solution was incubated at 50° C. for 1 hour to obtain a DNA sample. The DNA yield in each of the thus obtained DNA samples was determined by fluoro-metry. The DNA quantitation by fluorometry was carried out by the following method.

To 1 µl of each obtained DNA sample was added 10 µl of 2M 3,5-diaminobenzoic acid.2HCl, and stirred, after which the reaction was carried out at 60° C. for 30 minutes. Then, 1 ml of a 0.6 N perchloric acid solution was added to the reaction solution and the fluorescence intensity (Ex=415 nm, Em=515 nm) was measured by means of a fluorescence detector. The amount of DNA in each DNA sample was calculated using a calibration curve obtained on the basis of measurement results obtained for DNA standard samples prepared from DNA of a known concentration.

Table 2 shows the DNA yield in each DNA sample.

TABLE 2

| Heat treatment conditions | | DNA yield (µg/slice) |
| --- | --- | --- |
| No heating (room temp.) | 2 min | 3.1 |
| | 10 min | 3.1 |
| 70° C. | 2 min | 6.2 |
| | 10 min | 8.6 |
| 80 ° C. | 2 min | 8.9 |
| | 10 min | 9.7 |
| 90° C. | 2 min | 10.2 |
| | 10 min | 8.9 |
| 100° C. | 2 min | 9.2 |
| | 10 min | 9.1 |

As is clear from the results shown in Table 2, the DNA yield attained by the heat treatment at 70° C. for 2 minutes or 10 minutes is twice or more as high as that attained by the standing at room temperature (i.e. no heat treatment), and the DNA yield attained by the heat treatment at 80° C., 90° C. or 100° C. is about 3 times or more as high as that attained by the standing at room temperature. Thus, it can be seen that the heat treatment markedly increases the DNA yield.

EXAMPLE 4

Change in the amount of DNA extracted from a paraffin-embedded tissue sample, by heat treatment Two tissue slices (thickness 10 µm, about 10 mm×20 mm) were cut out of a formaldehyde fixed and paraffin embedded human tissue sample (liver). Each tissue slice was placed in a 1.5-ml test tube, followed by adding thereto 1 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at ordinary temperature, and the supernatant was discarded to remove the paraffin. The above procedure was repeated once on the precipitate. Subsequently, 1 ml of ethanol was placed in each test tube and the resulting mixture was stirred with the aforesaid mixer and then centrifuged at 12,000 for 3 minutes at ordinary temperature, after which the supernatant was discarded to remove a slight amount of the remaining D-limonene. This procedure was repeated once on the precipitate, and the thus obtained pellet was dried. Then, 20 µl of 11 mM Tris-HCl buffer (pH 7.0, containing 0.55% SDS and 5.6 mM EDTA) was placed in each test tube, and only one of the test tubes was heated at 90° C. for 10 minutes. The other test tube was not heated. Each test tube was then subjected to centrifugation at 10,000 rpm for 5 minutes at ordinary temperature, and the supernatant was used as a DNA sample. Finally, using 0.5 µl of each of the thus obtained DNA samples, amplification reaction of the k-ras gene was carried out by the PCR method (conditions in the PCR method: 94° C. for 1 minute, 55° C. for 2 minutes, 72° C. for 3 minutes; 45 cycles).

FIG. 4 shows the result of fluorometric detection of DNA carried out by means of a UV illuminator after electrophoresis of the DNA amplified by the PCR method, at a constant voltage of 100 V for 20 to 30 minutes on a 2.5% agarose gel prepared by use of 1×TAE buffer (0.04M Tris-acetate, 1 mM EDTA, pH 7.8) containing 0.5 g/ml of ethidium bromide. In FIG. 4, lane 1 shows the result obtained for a molecular weight marker (φ×174 phage DNA/HaeIII, mfd. by Nippon Gene Co., Ltd.). Lane 2 shows the result obtained for the DNA sample obtained without heat treatment, and lane 3 shows the result obtained for the DNA sample obtained by the heat treatment. In FIG. 4, the mark ← indicates the amplification region (108 bp) of the k-ras gene.

As is clear from the results shown in FIG. 4, when the result obtained for the DNA sample obtained by the heat treatment (lane 3) is compared with the result obtained for the DNA sample obtained without heat treatment (lane 2), the amount of the k-ras gene amplified is clearly larger in the case of the DNA sample obtained by the heat treatment. Thus, it can be seen that the sensitivity of the PCR analysis is increased, namely, the DNA yield is markedly increased in the case of the DNA sample obtained by the heat treatment.

EXAMPLE 5

Relation of heat treatment and protease treatment time to DNA yield

Ten tissue slices (thickness 10 µm, about 10 mm×20 mm) were cut out of a formaldehyde fixed and paraffin embedded human tissue sample (liver). Each tissue slice was placed in a 1.5-ml test tube, followed by adding thereto 1 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at ordinary temperature, and the supernatant was discarded to remove the paraffin. The above procedure was repeated once on the precipitate. Subsequently, 1 ml of ethanol was placed in each test tube and the resulting mixture was stirred with the aforesaid mixer and then centrifuged at 12,000 for 3 minutes at ordinary temperature, after which the supernatant was discarded to remove a slight amount of the remaining D-limonene. This procedure was repeated once on the precipitate, and the thus obtained pellet was dried. Then, 180 μl of 11 mM Tris-HCl buffer (pH 7.0, containing 0.55% SDS and 5.6 mM EDTA) was placed in each test tube, and five of the 10 test tubes was heated at 90° C. for 10 minutes. Thereafter, 20 μl of 1M DTT and 10 μl of a 20 mg/ml papain solution were placed in each of the 5 test tubes, and in these test tubes, the reaction was carried out at 50° C. for 0.5, 1.5, 5, 23 or 31 hours, respectively. The remaining 5 test tubes were not heated, and 20 μl of 1M DTT and 10 μl of a 20 mg/ml papain solution were placed in each of these test tubes, after which in these test tubes, the reaction was carried out at 50° C. for 0.5, 1.5, 5, 23 or 31 hours, respectively. After completion of the reaction in each of the 10 test tubes, 200 μl of a 40% (V/V) aqueous isopropanol solution (pH 6.0) containing 10% (W/V) m-hydroxybenzoic acid was added to the reaction solution, and the resulting solution was subjected to reaction at room temperature for 30 minutes. The thus obtained reaction solution was centrifuged at 12,000 rpm for 5 minutes and the supernatant was transferred into another tube by decantation. With the supernatant were mixed 40 μl of a 3M aqueous NaCl solution and 900 μl of isopropanol, and the resulting mixture was allowed to stand at room temperature for 10 minutes. Each test tube was subjected to centrifugation at 12,000 rpm for 15 minutes to precipitate nucleic acid. The supernatant was discarded and 1 ml of 70% ethanol was added to the precipitate and stirred, after which the resulting mixture was centrifuged at 15,000 rpm for 5 minutes at 4° C. Then, the supernatant was discarded and the precipitate was dried to obtain the desired nucleic acid. Finally, the obtained nucleic acid were redissolved in 20 μl of TE buffer (10 mM Tris-HCl buffer, containing 1 mM EDTA, pH 8.0), followed by adding thereto 1 μl of 10 mg/ml RNase, and the resulting solution was incubated at 50° C. for 1 hour to obtain a DNA sample. The DNA yield in each of the thus obtained DNA samples was determined by fluorometry. The DNA quantitation by fluorometry was carried out by the following method.

To 1 μl of each obtained DNA sample was added 10 μl of 2M 3,5-diaminobenzoic acid-2HCl, and stirred, after which the reaction was carried out at 60° C. for 30 minutes. Then, 1 ml of a 0.6N perchloric acid solution was added to the reaction solution and the fluorescence intensity (Ex=415 nm, Em=515 nm) was measured by means of a fluorescence detector. The amount of DNA in each DNA sample was calculated using a calibration curve obtained on the basis of measurement results obtained for DNA standard samples prepared from DNA of a known concentration.

Figure 5:
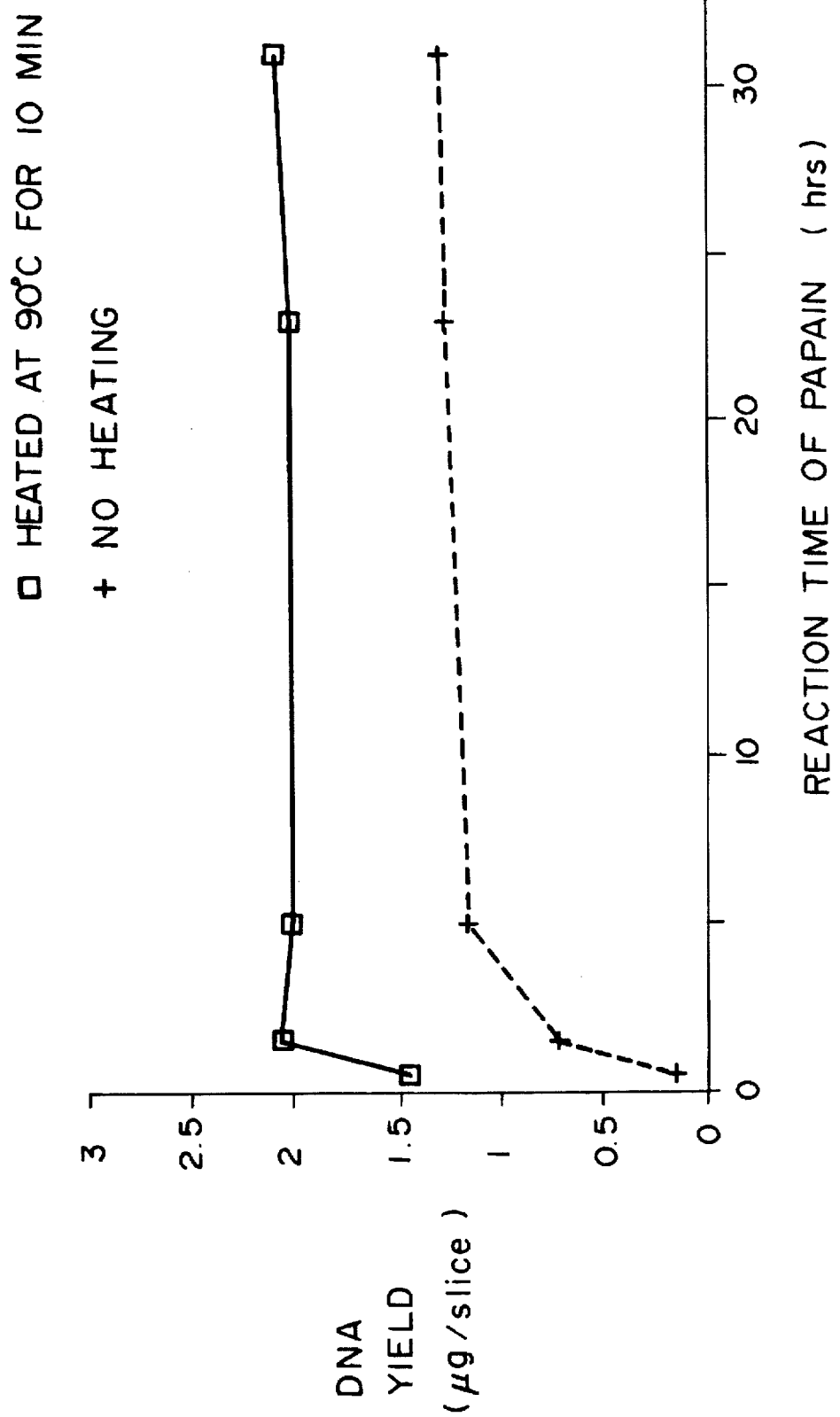
FIG. 5 is a graph showing the relationship between the amount of DNA in each DNA sample and protease treatment time which was determined in Example 5.

Table 3 shows the DNA yield in each DNA sample. FIG. 5 shows the relationship between the protease treatment time and the DNA yield. In FIG. 5, –□– shows the results obtained when the heat treatment was carried out, followed by the protease treatment, and –+– the results obtained when the protease treatment was carried out without heat treatment.

TABLE 3

| Protease treatment time (hrs) | DNA yield (μg/slice) | |
|---|---|---|
| | No heat treatment | Heated at 90° C. for 10 min. |
| 0.5 | 0.16 | 1.45 |
| 1.5 | 0.71 | 2.06 |
| 5 | 1.16 | 2.01 |
| 23 | 1.27 | 2.03 |
| 31 | 1.30 | 2.09 |

As is clear from the results shown in Table 3 and FIG. 5, when the protease treatment was carried out after the heat treatment at 90° C. for 10 minutes, the DNA yield reached 2.06 μg/slice after 1.5 hours of the protease treatment. On the other hand, when the protease treatment was carried out without heat treatment, DNA was obtained in an amount of only 1.30 μg/slice by the protease treatment for 31 hours. It can also be seen that when the protease treatment was carried out after the heat treatment had been carried out at 90° C. for 10 minutes, the protease treatment for only 0.5 hour made it possible to obtain DNA in an amount equal to or larger than that attained when the protease treatment was carried out for 31 hours without heat treatment.

From the above, it can be seen that by carrying out the protease treatment after carrying out the heat treatment by use of the surfactant having a protein-denaturational action, the operation time can be greatly reduced and the DNA yield can be greatly increased, as compared with the known method.

EXAMPLE 6

Change in the amount of DNA extracted, by addition of surfactant (SDS)

Four tissue slices (thickness 10 μm, about 8 mm×5 mm) were cut out of a formaldehyde fixed and paraffin embedded human tissue sample (liver). Each tissue slice was placed in a 0.5-ml test tube, followed by adding thereto 0.5 ml of D-limonene, and the resulting mixture was stirred with a micro-tube mixer (MT-360, mfd. by Tomy Seiko Co., Ltd.) for 3 minutes. The mixture was then centrifuged at 12,000 rpm for 3 minutes at ordinary temperature, and the supernatant was discarded to remove the paraffin. Subsequently, 0.5 ml of ethanol was placed in each test tube and the resulting mixture was stirred with the aforesaid mixer and then centrifuged at 12,000 for 3 minutes at ordinary temperature, after which the supernatant was discarded to remove a slight amount of the remaining D-limonene. The thus obtained pellet was dried. Then, 20 μl of 10 mM Tris-HCl buffer (pH 7.0, containing 5.6 mM EDTA) was placed in each of two of the four test tubes, and one of the two test tubes was allowed to stand at room temperature for 10 minutes. In each of the remaining two test tubes was placed 20 μl of 10 mM Tris-HCl buffer (pH 7.0, containing 0.55% SDS and 5.6 mM EDTA), and one of these two test tubes was allowed to stand at room temperature for 10 minutes. The other of them was heated at 90° C. for 10 minutes. Each of the four test tubes was then subjected to centrifugation at 10,000 rpm for 5 minutes at ordinary temperature, and the resulting supernatant was used as a DNA sample. Finally, using 4 μl of each of the thus obtained DNA samples, amplification reaction of the k-ras gene was carried out by the PCR method (conditions in the PCR method: 94° C. for 1 minute, 55° C. for 2 minutes, 72° C. for 3 minutes; 45 cycles).

Figure 6:
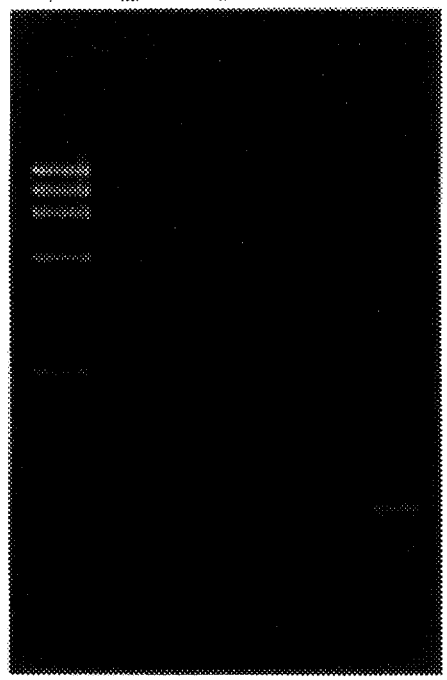
FIG. 6 is a photograph showing the results of 2.5% agarose gel electrophoresis of each DNA sample obtained in Example 6 which was carried out after amplification of the DNA sample by the PCR method.

The DNA amplified by the PCR method was electrophoresed at a constant voltage of 100 V for 20 to 30 minutes on a 2.5% agarose gel prepared by use of 1×TAE buffer (0.04M Tris-acetate, 1 mM EDTA, pH 7.8) containing 0.5 g/ml of ethidium bromide. Thereafter, fluorometric detection of the DNA was carried out by means of a UV illuminator. The results obtained are shown in FIG. 6. In FIG. 6, lane 1 shows the result obtained for a molecular weight marker (φ×174 phage DNA/Hae III, mfd. by Nippon Gene Co., Ltd.). Lane 2 shows the result obtained for the DNA sample obtained by use of the buffer containing no surfactant (SDS), without heat treatment. Lane 3 shows the result obtained for the DNA sample obtained by using the buffer containing no surfactant (SDS), and carrying out the heat treatment. Lane 4 shows the result obtained for the DNA sample obtained by use of the surfactant (SDS)-containing buffer without heat treatment. Lane 5 shows the result obtained for the DNA sample obtained by using the surfactant (SDS)-containing buffer and carrying out the heat treatment. In FIG. 6, the mark ← indicates the amplification region (108 bp) of the k-ras gene.

As is clear from the results shown in FIG. 6, substantially no amplified fragment of the k-ras gene was observed when there was used either the DNA sample obtained by use of the buffer containing no surfactant, without heat treatment (lane 2) or the DNA sample obtained by using the buffer containing no surfactant, and carrying out the heat treatment (lane 3). That is, when the buffer containing no surfactant was used, the DNA yield in the obtained DNA sample was low and was hardly dependent on whether the heat treatment was carried out. When there was used the DNA sample obtained by use of the surfactant-containing buffer without heat treatment (lane 4), substantially no amplified fragment of the k-ras gene was observed. On the other hand, when there was used the DNA sample obtained by using the surfactant-containing buffer and carrying out the heat treatment (lane 5), amplified fragments of the k-ras gene were clearly observed. That is, when the surfactant-containing buffer was used, the DNA yield in the obtained DNA sample could be markedly increased by the heat treatment. In addition, when the result obtained for the DNA sample obtained by using the surfactant-containing buffer and carrying out the heat treatment (lane 5) is compared with the result obtained for the DNA sample obtained by using the buffer containing no surfactant, and carrying out the heat treatment (lane 3), it can be seen that in the case of lane 5, the amount of the k-ras gene amplified is clearly larger, namely, the sensitivity of the PCR analysis is increased. Thus, it can be seen that the presence of the surfactant in the heat treatment markedly increases the DNA yield in the obtained DNA sample.

From the above, it can be seen that a sample for a gene analysis can easily be obtained by heat-treating a sample obtained from a paraffin-embedded tissue, by use of the surfactant.

As described above, the present invention provides a process for treating a paraffin-embedded tissue sample useful for a gene analysis and a treating kit used for practicing said process. When a paraffin-embedded tissue sample useful for a gene analysis is treated by utilizing the present invention, the following effects can be obtained: as compared with conventional treating processes, operations are simpler and the time required for practicing the process of the present invention is much shorter; and moreover contamination with impurities, in particular, contamination with substances inhibitory to the reaction carried out by the PCR method is slight, so that there can be obtained nucleic acid suitable as a sample for a pathological examination, a gene analysis, etc., which utilize the PCR method. Therefore, the present invention contributes greatly to the art.

Hydroxybenzoic acid used in the present invention as one of the organic compounds having a protein-denaturational action is an organic compound having one or more phenolic hydroxyl groups, is widely used as a fungicide for food and drink, and is not corrosive to a human body. No attempt has been made at all to use hydroxybenzoic acid as a protein denaturing agent in a process for treating a paraffin-embedded tissue sample useful for a gene analysis in which the two-phase separation method is not employed.

What is claimed is:

1. A process for treating a paraffin-embedded tissue sample to be used for a gene analysis, which comprises
heating an aqueous suspension containing a surfactant having a protein-denaturational action and a deparaffinized tissue sample obtained from a paraffin-embedded tissue sample at 60° C. or higher,
reacting the heat-treated aqueous suspension with a protease,
mixing the resulting reaction solution with a solution containing hydroxybenzoic acid.

2. A process for treating a paraffin-embedded tissue sample to be used for a gene analysis, which comprises
heating an aqueous suspension containing a surfactant having a protein-denaturational action and a deparaffinized tissue sample obtained from a paraffin-embedded tissue sample at 60° C. or higher.

3. A process according to claim 2, wherein heating is carried out at 70° C. to a boiling point of the aqueous suspension.

4. A process for treating a paraffin-embedded tissue sample to be used for a gene analysis, which comprises
heating an aqueous suspension containing a surfactant having a protein-denaturational action and a deparaffinized tissue sample obtained from a paraffin-embedded tissue sample at 60° C. or higher, and
reacting the heat-treated aqueous suspension with a protease.

5. A process for treating a paraffin-embedded tissue sample to be used for a gene analysis, which comprises
heating an aqueous suspension containing a surfactant having a protein-denaturational action and a deparaffinized tissue sample obtained from a paraffin-embedded tissue sample at 60° C. or higher,
reacting the heat-treated aqueous suspension with a protease, and
precipitating a nucleic acid from the resulting reaction solution.

6. A process for treating a paraffin-embedded tissue sample to be used for a gene analysis, which comprises
heating an aqueous suspension containing a surfactant having a protein-denaturational action and a deparaffinized tissue sample obtained from a paraffin-embedded tissue sample at 60° C. or higher,
reacting the heat-treated aqueous suspension with a protease,
mixing the resulting reaction solution with a solution containing an organic compound having a protein-denaturational action other than the surfactant mentioned above, and
precipitating a nucleic acid from the resulting reaction solution.

7. A process according to claim 5, wherein the solution containing an organic compound is an aqueous alcoholic solution containing an organic compound having one or more phenolic hydroxyl groups.

8. A kit for treating a paraffin-embedded tissue sample to be used for a gene analysis, which comprises a container containing a surfactant having a protein-denaturational action, a container containing a protease, and a container containing a hydroxybenzoic acid solution.

9. A kit according to claim 8, wherein the surfactant is sodium dodecylsulfate and the protease is papain.

10. A process for treating a paraffin-embedded tissue sample to be used for a gene analysis, which comprises heating an aqueous suspension containing a surfactant having a protein-denaturational action and a deparaffinized tissue sample obtained from a paraffin-embedded tissue sample, reacting the heat-treated aqueous suspension with a protease, mixing the resulting reaction solution with an aqueous alcoholic solution containing hydroxybenzoic acid, and precipitating a nucleic acid from the resulting reaction solution.

* * * * *

UNITED STATES PATENT AND TRADEMARK OFFICE
CERTIFICATE OF CORRECTION

PATENT NO.: 5,672,696
DATED     : Sep. 30, 1997
INVENTOR(S): WANG et al.

It is certified that error appears in the above-identified patent and that said Letters Patent is hereby corrected as shown below:

Column 20, line 66, delete "5" and substitute therefor --6--.

Signed and Sealed this

Twenty-fourth Day of March, 1998

Attest:

BRUCE LEHMAN

Attesting Officer

Commissioner of Patents and Trademarks